US011702465B1

(12) United States Patent
Lillo et al.

(10) Patent No.: US 11,702,465 B1
(45) Date of Patent: Jul. 18, 2023

(54) SYNTHETIC ANTI-PLAGUE ANTIBODIES

(71) Applicant: Triad National Security, LLC, Los Alamos, NM (US)

(72) Inventors: Antonietta Maria Lillo, Los Alamos, NM (US); Nileena Velappan, Los Alamos, NM (US); Armand Earl Ko Dichosa, Los Alamos, NM (US); Stosh Anthony Kozimor, Los Alamos, NM (US); Laura Margaret Lilley, Los Alamos, NM (US)

(73) Assignee: Triad National Security, LLC, Los Alamos, NM (US)

( * ) Notice: Subject to any disclaimer, the term of this patent is extended or adjusted under 35 U.S.C. 154(b) by 424 days.

(21) Appl. No.: 17/033,516

(22) Filed: Sep. 25, 2020

Related U.S. Application Data

(60) Provisional application No. 62/905,858, filed on Sep. 25, 2019.

(51) Int. Cl.
| | |
|---|---|
| *C07K 16/12* | (2006.01) |
| *A61K 51/10* | (2006.01) |
| *A61P 31/06* | (2006.01) |
| *G01N 33/569* | (2006.01) |
| *A61K 39/00* | (2006.01) |

(52) U.S. Cl.
CPC ...... *C07K 16/1228* (2013.01); *A61K 51/1009* (2013.01); *A61P 31/06* (2018.01); *G01N 33/56916* (2013.01); *A61K 2039/505* (2013.01); *C07K 2317/565* (2013.01); *C07K 2317/76* (2013.01); *C07K 2317/92* (2013.01); *C07K 2317/94* (2013.01); *C07K 2319/30* (2013.01); *G01N 2800/26* (2013.01)

(58) Field of Classification Search
CPC .......... C07K 16/1228; C07K 2317/565; C07K 2317/76; C07K 2317/92; C07K 2317/94; C07K 2319/30; A61K 51/1009; A61K 2039/505; A61P 31/06; G01N 33/56916; G01N 2800/26
See application file for complete search history.

(56) References Cited

PUBLICATIONS

Lillo et al., "Development of Phage-Based Single Chain Fv Antibody Reagents for Detection of Yersinia pestis," *PLoS ONE*, vol. 6:e27756, 2011.

*Primary Examiner* — Adam Weidner
*Assistant Examiner* — Laura Ann Essex
(74) *Attorney, Agent, or Firm* — Klarquist Sparkman, LLP

(57) ABSTRACT

Monoclonal antibodies that specifically bind the F1 antigen of *Yersinia pestis* with high affinity are described. Use of the monoclonal antibodies for the detection of *Y. pestis* infection and the diagnosis of plague are also described. Immunoconjugates of the monoclonal antibodies and a radionuclide can also be used for the treatment of a *Y. pestis* infection.

22 Claims, 7 Drawing Sheets

Specification includes a Sequence Listing.

FIG. 1A
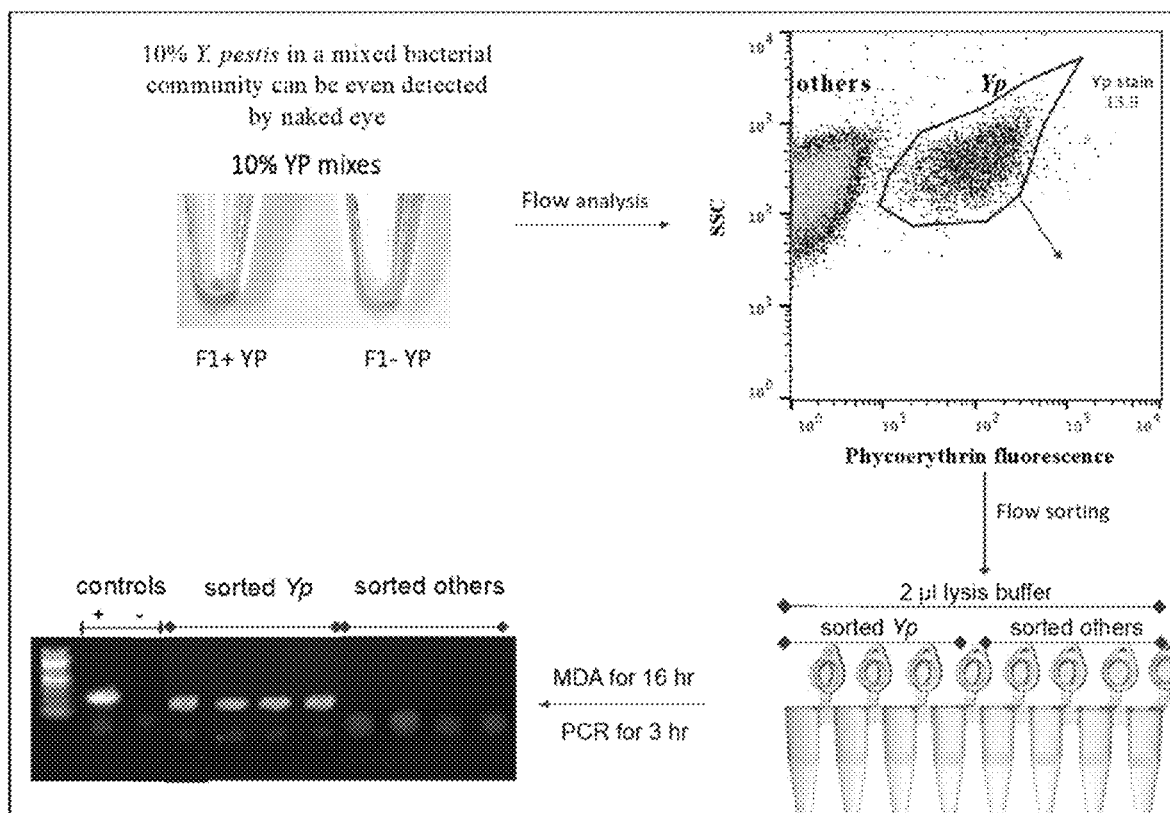
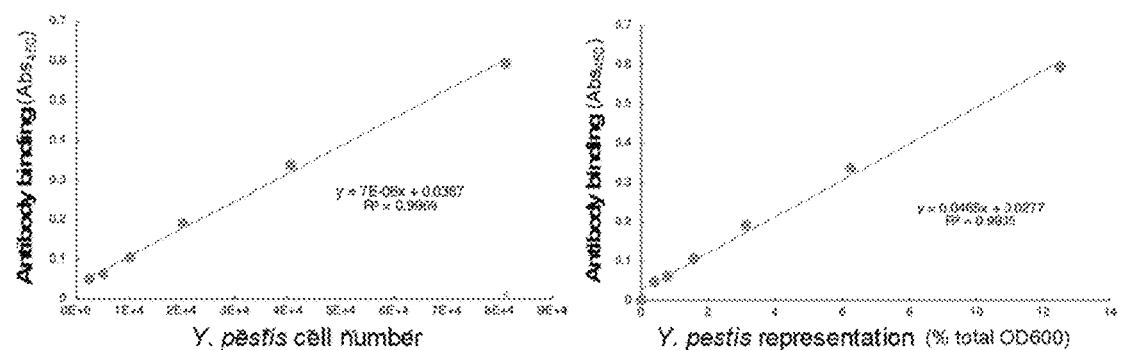
FIG. 1B

SYNTHETIC ANTI-PLAGUE ANTIBODIES

CROSS REFERENCE TO RELATED APPLICATIONS

This application claims the benefit of U.S. Provisional Application No. 62/905,858, filed Sep. 25, 2019, which is herein incorporated by reference in its entirety.

ACKNOWLEDGMENT OF GOVERNMENT SUPPORT

This invention was made with government support under Contract No. 89233218CNA000001 awarded by the U.S. Department of Energy/National Nuclear Security Administration. The government has certain rights in the invention.

FIELD

This disclosure concerns affinity matured human monoclonal antibodies that specifically bind two different epitopes of Yersinia pestis F1 antigen with high affinity, and use of the antibodies for therapeutic and diagnostic applications.

BACKGROUND

Yersinia pestis is a gram-negative, non-spore-forming bacterium belonging to the family Enterobacteriaceae that is known to have evolved from the enteric pathogen Yersinia pseudotuberculosis approximately 20,000 years ago (Achtman et al., Proc Nat Acad Sci USA 96: 14043-14048, 1999). Among the eleven true Yersinia species, three are pathogenic to humans: Yersinia pestis, Yersinia pseudotuberculosis and Yersinia enterocolytica, while all others are harmless (Perry et al., Clin Microbiol Rev 10: 35-66, 1997). Y. pestis is the causative agent of the plague; an illness that manifests itself in bubonic, pneumonic or septicemic forms that have resulted in the death of an estimated 200 million people throughout history (Perry et al., Clin Microbiol Rev 10: 35-66, 1997). Once aerosolized, the infectious agent can be dispersed and transmitted via inhalation causing pneumonic plague, the least common but most virulent form, which has the potential to cause high rates of morbidity and mortality in humans.

SUMMARY

Two affinity matured (AM) monoclonal antibodies that bind different epitopes of the Yersinia pestis F1 antigen are disclosed. The antibodies bind F1 with high (picomolar) affinity. The disclosed antibodies can be used for both detection of Y. pestis in a sample and therapeutic purposes.

Monoclonal antibodies that specifically bind Y. pestis F1 antigen are provided. In some embodiments, the monoclonal antibody includes a variable light (VL) domain and a variable heavy (VH) domain and possesses the CDR sequences of antibody AM IgG B or AM IgG H, as disclosed herein. The CDR sequences can be determined using any method known in the art, such as the Kabat, IMGT or Chothia method. In some examples, the CDR sequences are determined using the method of Kabat. In some examples, the monoclonal antibody is an antigen-binding fragment, such as a single chain fragment variable (scFv). In other examples, the monoclonal antibody is an immunoglobulin G (IgG), such as IgG1.

Also provided are immunoconjugates that include a monoclonal antibody disclosed herein and an effector molecule. In some examples, the effector molecule is a detectable label, such as a fluorophore or an enzyme. In other examples, the effector molecule is a radionuclide, such as a radionuclide bound to a chelator.

Further provided are fusion proteins that include a monoclonal antibody disclosed herein and a heterologous protein or peptide.

Nucleic acid molecules and vectors encoding a disclosed monoclonal antibody or fusion protein are also provided.

Also provided are compositions that include a monoclonal antibody, immunoconjugate or fusion protein disclosed herein, and a pharmaceutically acceptable carrier.

Further provided are methods of treating a Y. pestis infection and/or plague in a subject by administering to the subject a therapeutically effective amount of a monoclonal antibody, immunoconjugate, fusion protein or composition disclosed herein.

Methods of detecting Yersinia pestis in a sample by contacting a sample with a monoclonal antibody or immunoconjugate disclosed herein and detecting binding of the monoclonal antibody or the immunoconjugate to the sample, are also provided. In some embodiments, the detection is performed using a lateral flow assay (LFA). In some embodiments, the sample is a blood, serum, lymph node aspirate or sputum sample.

The foregoing and other objects and features of the disclosure will become more apparent from the following detailed description, which proceeds with reference to the accompanying figures.

BRIEF DESCRIPTION OF THE DRAWINGS

FIGS. 1A-1B: Antibody specificity for F1-positive Y. pestis. (FIG. 1A) Flow cytometry analysis and genetic analysis of a mixed community shows that the antibodies target Y. pestis selectively. A mixed population of E. coli, Y. pseudotuberculosis, B. anthracis, P. fluorescence and Y. pestis was stained with phycoerythrin-labelled anti-F1 IgG B. The percentage of stained cells (13.5%) matched Y. pestis representation (10%) within error. Furthermore, single PE-labelled cells tested positive by PCR amplification of Y. pestis-specific genomic region YpA, whereas unstained cells did not. (FIG. 1B) Enzyme-linked immunosorbent assay (ELISA) analysis of a mixed community confirms specificity of the antibodies for Y. pestis. Samples of the same mixed community used for FIG. 1A with different Y. pestis representation was analyzed by whole-cell ELISA. ELISA signals (absorbance at 450 nm caused by antibody binding) were directly proportional to the number of Y. pestis in the mixed community. A minimum of one thousand cells corresponding to 0.4% of the entire population could be detected.

(FIG. 2A) Intrinsically fluorescent scFp B (antibody B single chain (scFv)-GFP chimera) bound to purified antigen F1 is not displaced by IgG H but it is by IgG B. (FIG. 2B) IgG B-PE binds to Y. pestis with the same affinity (same $K_D$, within error) in the presence or absence of saturating concentration of unlabeled IgG H. (FIG. 2C) Cells captured by immobilized antibody B or antibody H and saturated with the same antibody still bind to HRP conjugated antibody H or antibody B, respectively, albeit with lower affinity (higher $K_D$) than their unconjugated counterpart.

(FIG. 4A): 1=10 ng; 2=7 ng; 3=5 ng. (FIG. 4B): 1=3.5×10⁵ cells; 2=2×10⁵ cells; 3=1×10⁵ cells; 4=7×10⁴ cells.

(FIG. 5A) Antibody solutions (0.9 mg/mL in PBS, no preservatives) were incubated at 37° C. over a period of 60 days, and periodically analyzed by DLS. Variations in particle size were within the margin of error during this period, indicating the antibodies were stable. (FIG. 5B) The same antibody solutions were subjected to various temperatures starting at 37° C., and analyzed by DLS after an equilibration time of 3 minutes. The lack of signal at 45° C. (AM IgG B) and 51° C. (AM IgG H) signifies a lower-than-detectable amount of particle, which is likely due to particle aggregation.

SEQUENCE LISTING

Figure 2A:
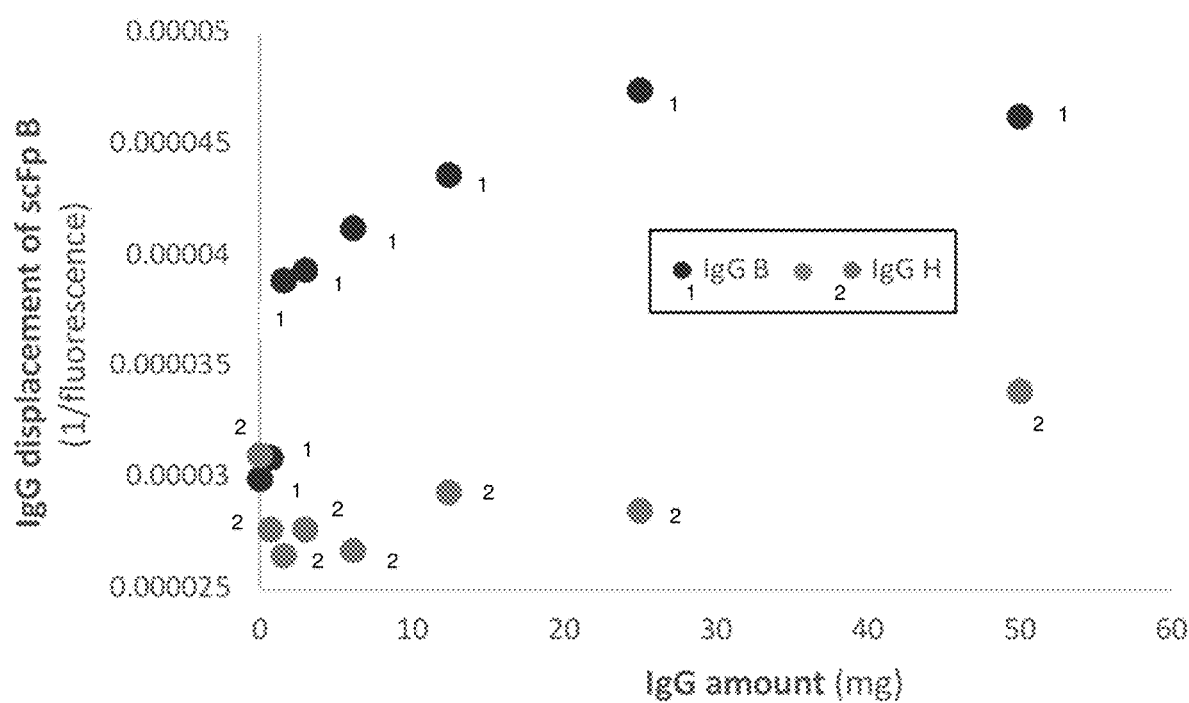
FIGS. 2A-2C: The F1-specific antibodies target two different epitopes of the F1 antigen. The binding of antibody B and antibody H to purified or cell-expressed F1 is non-competitive as shown by fluorescence-linked immunosorbent assay (FLISA) (FIG. 2A), flow cytometry (FIG. 2B), and sandwich ELISA (FIG. 2C).

The amino acid sequences listed in the accompanying sequence listing are shown using standard three letter code for amino acids, as defined in 37 C.F.R. 1.822. The Sequence Listing is submitted as an ASCII text file, created on Sep. 18, 2020, 11.6 KB, which is incorporated by reference herein. In the accompanying sequence listing:

SEQ ID NO: 1 is the amino acid sequence of the (kappa) light chain of the AM IgG B antibody. CDRs (Kabat) are indicated in bold. Mutations resulting from affinity maturation are underlined.

DIRMTQSPSSLSASVGDRVTITCRASRSISGYLNWYQQKPGKAPKLLI

YATSSLQSGVPSRFSGSGSGTDFTLTISSLQPEDFATYYCQQSYSTPS

SFGQGTKVDIKRTVAAPSVFIFPPSDEQLKSGTASVVCLLNNFYPREA

KVQWKVDNALQSGNSQESVTEQDSKDSTYSLSSTLTLSKADYEKHKVY

ACEVTHQGLSSPVTKSFNRGEC

Residues 1-107=VL domain
Residues 24-34=CDR1
Residues 50-56=CDR2
Residues 90-97=CDR3

SEQ ID NO: 2 is the amino acid sequence of the heavy chain of the AM IgG B antibody. CDRs (Kabat) are indicated in bold. Mutations resulting from affinity maturation are underlined.

QVQLVESGGGLVKPGGSLRLSCAASGFTFSDYYMSWIRQAPGKGLEWV

SYISGSGSIIYYADSVKGRFTISRDNAKNSLYLQMNSLRAEDTAVYYC

AKEIRKHDAFDIWGQGTMVTVSSASTKGPSVFPLAPSSKSTSGGTAAL

GCLVKDYFPEPVTVSWNSGALTSGVHTFPAVLQSSGLYSLSSVVTVPS

SSLGTQTYICNVNHKPSNTKVDKKVEPKSCDKTHTCPPCPAPELLGGP

SVFLFPPKPKDTLMISRTPEVTCVVVDVSHEDPEVKFNWYVDGVEVHN

AKTKPREEQYNSTYRVVSVLTVLHQDWLNGKEYKCKVSNKALPAPIEK

TISKAKGQPREPQVYTLPPSRDELTKNQVSLTCLVKGFYPSDIAVEWE

SNGQPENNYKTTPPVLDSDGSFFLYSKLTVDKSRWQQGNVFSCSVMHE

ALHNHYTQKSLSLSPGK

Residues 1-119=VH domain
Residues 26-35=CDR1
Residues 52-60=CDR2
Residues 100-108=CDR3

SEQ ID NO: 3 is the amino acid sequence of the (lambda) light chain of the AM IgG H antibody. CDRs (Kabat) are indicated in bold. Mutations resulting from affinity maturation are underlined.

QPVLTQSPSVSVSPGQTASITCSGDKLGGRYASWYQQKPGQSPVLVI

YQDTKRPSGIPERFSGSNSGNTATLTISGTQAMDEADYYCQSWDSSA

AVFGTGTKLTVLGQPKAAPSVTLFPPSSEELQANKATLVCLISDFYP

GAVTVAWKADSSPVKAGVETTTPSKQSNNKYAASSYLSLTPEQWKSH

KSYSCQVTHEGSTVEKTVAPTECS

Residues 1-106=VL domain
Residues 23-33=CDR1
Residues 49-55=CDR2
Residues 88-96=CDR3

SEQ ID NO: 4 is the amino acid sequence of the heavy chain of the AM IgG H AM antibody. CDRs (Kabat) are indicated in bold. Mutations resulting from affinity maturation are underlined.

QVQLQQWGAGLLKPSETLSLTCAVYGGSFSGYYWSWIRQPPGKGLEWI

GEINRSGNTNYNPSLKSRVTISVDTSKNQFSLQLNSVTPEDTAVYYCA

RTRGYFDLWGRGTLVTVSSASTKGPSVFPLAPSSKSTSGGTAALGCLV

KDYFPEPVTVSWNSGALTSGVHTFPAVLQSSGLYSLSSVVTVPSSSLG

TQTYICNVNHKPSNTKVDKKVEPKSCDKTHTCPPCPAPELLGGPSVFL

FPPKPKDTLMISRTPEVTCVVVDVSHEDPEVKFNWYVDGVEVHNAKTK

PREEQYNSTYRVVSVLTVLHQDWLNGKEYKCKVSNKALPAPIEKTISK

AKGQPREPQVYTLPPSRDELTKNQVSLTCLVKGFYPSDIAVEWESNGQ

PENNYKTTPPVLDSDGSFFLYSKLTVDKSRWQQGNVFSCSVMHEALHN

HYTQKSLSLSPGK

Residues 1-115=VH domain
Residues 26-35=CDR1
Residues 52-59=CDR2
Residues 98-104=CDR3

DETAILED DESCRIPTION

I. Terms

Unless otherwise noted, technical terms are used according to conventional usage. Definitions of common terms in molecular biology may be found in Benjamin Lewin, *Genes X*, published by Jones & Bartlett Publishers, 2009; and Meyers et al. (eds.), *The Encyclopedia of Cell Biology and*

*Molecular Medicine*, published by Wiley-VCH in 16 volumes, 2008; and other similar references.

As used herein, the singular forms "a," "an," and "the," refer to both the singular as well as plural, unless the context clearly indicates otherwise. For example, the term "an antigen" includes single or plural antigens and can be considered equivalent to the phrase "at least one antigen." As used herein, the term "comprises" means "includes." It is further to be understood that any and all base sizes or amino acid sizes, and all molecular weight or molecular mass values, given for nucleic acids or polypeptides are approximate, and are provided for descriptive purposes, unless otherwise indicated. Although many methods and materials similar or equivalent to those described herein can be used, particular suitable methods and materials are described herein. In case of conflict, the present specification, including explanations of terms, will control. In addition, the materials, methods, and examples are illustrative only and not intended to be limiting. To facilitate review of the various embodiments, the following explanations of terms are provided: Antibody: A polypeptide ligand comprising at least one variable region that recognizes and binds (such as specifically recognizes and specifically binds) an epitope of an antigen.

Mammalian immunoglobulin molecules are composed of a heavy (H) chain and a light (L) chain, each of which has a variable region, termed the variable heavy ($V_H$) region and the variable light ($V_L$) region, respectively. Together, the VH region and the $V_L$ region are responsible for binding the antigen recognized by the antibody. There are five main heavy chain classes (or isotypes) of mammalian immunoglobulin, which determine the functional activity of an antibody molecule: IgM, IgD, IgG, IgA and IgE. Antibody isotypes not found in mammals include IgX, IgY, IgW and IgNAR. IgY is the primary antibody produced by birds and reptiles, and is functionally similar to mammalian IgG and IgE. IgW and IgNAR antibodies are produced by cartilaginous fish, while IgX antibodies are found in amphibians.

Antibody variable regions contain "framework" regions and hypervariable regions, known as "complementarity determining regions" or "CDRs." The CDRs are primarily responsible for binding to an epitope of an antigen. The framework regions of an antibody serve to position and align the CDRs in three-dimensional space. The amino acid sequence boundaries of a given CDR can be readily determined using any of a number of well-known numbering schemes, including those described by Kabat et al. (*Sequences of Proteins of Immunological Interest*, U.S. Department of Health and Human Services, 1991; the "Kabat" numbering scheme), Chothia et al. (see Chothia and Lesk, *J Mol Biol* 196:901-917, 1987; Chothia et al., *Nature* 342:877, 1989; and Al-Lazikani et al., JMB 273,927-948, 1997; the "Chothia" numbering scheme), Kunik et al. (see Kunik et al., *PLoS Comput Biol* 8:e1002388, 2012; and Kunik et al., *Nucleic Acids Res* 40 (Web Server issue):W521-524, 2012; "Paratome CDRs") and the ImMunoGeneTics (IMGT) database (see, Lefranc, *Nucleic Acids Res* 29:207-9, 2001; the "IMGT" numbering scheme). The Kabat, Paratome and IMGT databases are maintained online.

A "single-domain antibody" refers to an antibody having a single domain (a variable domain) that is capable of specifically binding an antigen, or an epitope of an antigen, in the absence of an additional antibody domain. Single-domain antibodies include, for example, VH domain antibodies, $V_{NAR}$ antibodies, camelid $V_HH$ antibodies, and $V_L$ domain antibodies. $V_{NAR}$ antibodies are produced by cartilaginous fish, such as nurse sharks, wobbegong sharks, spiny dogfish and bamboo sharks. Camelid $V_HH$ antibodies are produced by several species including camel, llama, alpaca, dromedary, and guanaco, which produce heavy chain antibodies that are naturally devoid of light chains.

A "monoclonal antibody" is an antibody produced by a single clone of lymphocytes or by a cell into which the coding sequence of a single antibody has been transfected. Monoclonal antibodies are produced by methods known to those of skill in the art. Monoclonal antibodies include humanized monoclonal antibodies.

A "chimeric antibody" has framework residues from one species, such as human, and CDRs (which generally confer antigen binding) from another species.

A "humanized" antibody is an immunoglobulin including a human framework region and one or more CDRs from a non-human (for example a mouse, rabbit, rat, shark or synthetic) immunoglobulin. The non-human immunoglobulin providing the CDRs is termed a "donor," and the human immunoglobulin providing the framework is termed an "acceptor." In one embodiment, all CDRs are from the donor immunoglobulin in a humanized immunoglobulin. Constant regions need not be present, but if they are, they must be substantially identical to human immunoglobulin constant regions, i.e., at least about 85-90%, such as about 95% or more identical. Hence, all parts of a humanized immunoglobulin, except possibly the CDRs, are substantially identical to corresponding parts of natural human immunoglobulin sequences. A humanized antibody binds to the same antigen as the donor antibody that provides the CDRs. Humanized or other monoclonal antibodies can have additional conservative amino acid substitutions which have substantially no effect on antigen binding or other immunoglobulin functions.

Binding affinity: Affinity of an antibody for an antigen. In one embodiment, affinity is calculated by a modification of the Scatchard method described by Frankel et al., *Mol. Immunol.*, 16:101-106, 1979. In another embodiment, binding affinity is measured by an antigen/antibody dissociation rate. In another embodiment, a high binding affinity is measured by a competition radioimmunoassay. In another embodiment, binding affinity is measured by ELISA. In other embodiments, antibody affinity is measured by flow cytometry or by surface plasmon reference. An antibody that "specifically binds" an antigen (such as F1) is an antibody that binds the antigen with high affinity and does not significantly bind other unrelated antigens.

Chelator: A small molecule that binds very tightly to metal ions. Examples of chelators include, but are not limited to, diethylene-triamine-pentaacetic acid (DTPA), cyclohexane-diethylene-triamine-pentaacetic-acid (CHX-DTPA), DTPA derivatives such as p-isothiocyanatobenzyl-diethylenetriaminepentaacetic acid (p-SCN-Bz-DTPA), ethylenediamine-tetraacetic acid (EDTA), 1,4,7,10-tetraazacyclododecane-1,4,7,10-tetraacetic acid (DOTA), DOTA derivatives such as p-isothiocyanatobenzyl-1,4,7,10-tetraazacyclododecane-1,4,7,10-tetraacetic acid (p-SCN-Bz-DOTA), 1,4,7-triazacyclononane-N,N',N"-triacetetate (NOTA), ethylenediamine tetra(methylene phosphonic acid) (EDTMP), 1,4,7,10-tetraazacyclododecane-1,4,7,10-tetra (methylene phosphonic acid) (DOTMP), N-chloro-p-toluenesulfonamide, tetrachloro-3-6α-diphenylglycouril-3, (2-(4-isothiocyanatobenzyl-1,4,7,10-tetraaza-1,4,7,10,tetra-(2-carbamonyl-methyl)-cyclododecane) (TCMC), tris (hydroxypyridinone) (THP), and desferrioxamine (DFO).

Complementarity determining region (CDR): A region of hypervariable amino acid sequence that defines the binding affinity and specificity of an antibody. The light and heavy chains of a mammalian immunoglobulin each have three CDRs, designated L-CDR1, L-CDR2, L-CDR3 and H-CDR1, H-CDR2, H-CDR3, respectively. A single-domain antibody contains three CDRs, referred to herein as CDR1, CDR2 and CDR3.

Conjugate: In the context of the present disclosure, a "conjugate" is an antibody or antibody fragment (such as an antigen-binding fragment) covalently linked to an effector molecule or a second protein (such as a second antibody). The effector molecule can be, for example, a drug, toxin, therapeutic agent, detectable label, radionuclide, protein, nucleic acid, lipid, nanoparticle, photon absorber, carbohydrate or recombinant virus. An antibody conjugate is often referred to as an "immunoconjugate."

Contacting: Placement in direct physical association; includes both in solid and liquid form.

Diagnostic: Identifying the presence or nature of a pathologic condition, such as a $Y.\ pestis$ infection (e.g., plague). Diagnostic methods differ in their sensitivity and specificity. The "sensitivity" of a diagnostic assay is the percentage of diseased individuals who test positive (percent of true positives). The "specificity" of a diagnostic assay is one minus the false positive rate, where the false positive rate is defined as the proportion of those without the disease who test positive. While a particular diagnostic method may not provide a definitive diagnosis of a condition, it suffices if the method provides a positive indication that aids in diagnosis.

Effector molecule: The portion of a chimeric molecule that is intended to have a desired effect on a cell to which the chimeric molecule is targeted. Effector molecule is also known as an effector moiety (EM), therapeutic agent, diagnostic agent, or similar terms. Therapeutic agents (or drugs) include such compounds as nucleic acids, proteins, peptides, amino acids or derivatives, glycoproteins, radioisotopes, radionuclides, photon absorbers, lipids, carbohydrates, or recombinant viruses. Diagnostic agents or moieties include radioisotopes and other detectable labels. Detectable labels useful for such purposes are also well known in the art, and include radioactive isotopes such as $^{35}S$, $^{11}C$, $^{13}N$, $^{15}O$, $^{18}F$, $^{19}F$, $^{99m}Tc$, $^{131}I$, $^{3}H$, $^{14}C$, $^{15}N$, $^{90}Y$, $^{99}Tc$, $^{111}In$ and $^{125}I$, fluorophores, chemiluminescent agents, and enzymes.

Epitope: An antigenic determinant. These are particular chemical groups or peptide sequences on a molecule that are antigenic (that elicit a specific immune response). An antibody specifically binds a particular antigenic epitope on an antigen, such as F1.

Framework region: Amino acid sequences interposed between CDRs. Framework regions of an immunoglobulin molecule include variable light and variable heavy framework regions.

Fusion protein: A protein comprising at least a portion of two different (heterologous) proteins.

Heterologous: Originating from a separate genetic source or species.

Immunoconjugate: A covalent linkage of an effector molecule to an antibody or functional fragment thereof. The effector molecule can be, for example, a detectable label, a radionuclide, a photon absorber, or a toxin.

Isolated: An "isolated" biological component, such as a nucleic acid, protein (including antibodies) or organelle, has been substantially separated or purified away from other biological components in the environment (such as a cell) in which the component naturally occurs, for example other chromosomal and extra-chromosomal DNA and RNA, proteins and organelles.

Nucleic acids and proteins that have been "isolated" include nucleic acids and proteins purified by standard purification methods. The term also embraces nucleic acids and proteins prepared by recombinant expression in a host cell as well as chemically synthesized nucleic acids.

Label (or detectable label): A detectable compound or composition that is conjugated directly or indirectly to another molecule, such as an antibody or a protein, to facilitate detection of that molecule. Specific, non-limiting examples of labels include fluorescent tags, enzymatic linkages, radionuclides (such as radionuclides bound to a chelator) and radioactive isotopes. Examples of labels for polypeptides include, but are not limited to, the following: radioisotopes or radionuclides (such as $^{35}S$, $^{11}C$, $^{13}N$, $^{15}O$, $^{18}F$, $^{19}F$, $^{99m}Tc$, $^{131}I$, $^{3}H$, $^{14}C$, $^{15}N$, $^{90}Y$, $^{99}Tc$, $^{111}In$ and $^{125}I$), fluorescent labels (such as fluorescein isothiocyanate (FITC), rhodamine, lanthanide phosphors), enzymatic labels (such as horseradish peroxidase, beta-galactosidase, luciferase, alkaline phosphatase), chemiluminescent markers, biotinyl groups, predetermined polypeptide epitopes recognized by a secondary reporter (such as a leucine zipper pair sequences, binding sites for secondary antibodies, metal binding domains, epitope tags), or magnetic agents, such as gadolinium chelates. In some embodiments, labels are attached by spacer arms of various lengths to reduce potential steric hindrance.

Lateral flow assay (LFA): A paper-based assay for the detection and quantification of analytes in a sample. LFA is a simple, rapid, portable and low-cost detection method. The LFA paper strip typically includes an absorbent pad at one end where the sample is added, a conjugate release pad that contains labelled antibodies (e.g., anti-F1 antibody conjugated to gold nanoparticles) that bind the target analyte (e.g., the F1 antigen of $Y.\ pestis$), a nitrocellulose membrane comprising test line containing analyte-specific antibodies (e.g., anti-F1 antibody) and a control line that has antibodies specific for a control analyte (e.g., anti-IgG antibodies). To perform a LFA, the sample is applied to the absorbent pad and the sample moves along the paper strip through capillary action. If the analyte of interest is present in the sample, it will bind to the labelled analyte-specific antibodies and the anti-analyte antibodies located at the test line (see, e.g., Koczula and Estrela, *Essays Biochem* 60(1): 111-120, 2016; and Ma et al., *BMC Infect Dis* 19: 108, 2019).

Operably linked: A first nucleic acid sequence is operably linked with a second nucleic acid sequence when the first nucleic acid sequence is placed in a functional relationship with the second nucleic acid sequence. For instance, a promoter is operably linked to a coding sequence if the promoter affects the transcription or expression of the coding sequence. Generally, operably linked DNA sequences are contiguous and, where necessary to join two protein-coding regions, in the same reading frame.

Pharmaceutically acceptable carriers: The pharmaceutically acceptable carriers of use are conventional. *Remington: The Science and Practice of Pharmacy*, The University of the Sciences in Philadelphia, Editor, Lippincott, Williams, & Wilkins, Philadelphia, Pa., 21$^{st}$ Edition (2005), describes compositions and formulations suitable for pharmaceutical delivery of the antibodies and other compositions disclosed herein. In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. For solid compositions (such as powder, pill, tablet, or capsule forms), conventional non-toxic solid carriers can include, for example, pharmaceutical grades of mannitol, lactose, starch, or magnesium stearate. In addition to biologically neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

Preventing, treating or ameliorating a disease: "Preventing" a disease refers to inhibiting the full development of a disease. "Treating" refers to a therapeutic intervention that ameliorates a sign or symptom of a disease or pathological condition after it has begun to develop. "Ameliorating" refers to the reduction in the number or severity of signs or symptoms of a disease, such as plague.

Sample (or biological sample): A biological specimen containing genomic DNA, RNA (including mRNA), protein (such as antibodies), or combinations thereof, obtained from a subject. Examples include, but are not limited to, peripheral blood, plasma, sputum, tissue, cells, urine, saliva, tissue biopsy, fine needle aspirate (such as a lymph node aspirate), surgical specimen, and autopsy material.

Sequence identity: The similarity between amino acid or nucleic acid sequences is expressed in terms of the similarity between the sequences, otherwise referred to as sequence identity. Sequence identity is frequently measured in terms of percentage identity (or similarity or homology); the higher the percentage, the more similar the two sequences are. Homologs or variants of a polypeptide or nucleic acid molecule will possess a relatively high degree of sequence identity when aligned using standard methods.

Methods of alignment of sequences for comparison are well known in the art. Various programs and alignment algorithms are described in: Smith and Waterman, *Adv. Appl. Math.* 2:482, 1981; Needleman and Wunsch, *J. Mol. Biol.* 48:443, 1970; Pearson and Lipman, *Proc. Natl. Acad. Sci. U.S.A.* 85:2444, 1988; Higgins and Sharp, Gene 73:237, 1988; Higgins and Sharp, *CABIOS* 5:151, 1989; Corpet et al., *Nucleic Acids Research* 16:10881, 1988; and Pearson and Lipman, *Proc. Natl. Acad. Sci. U.S.A.* 85:2444, 1988. Altschul et al., *Nature Genet.* 6:119, 1994, presents a detailed consideration of sequence alignment methods and homology calculations.

The NCBI Basic Local Alignment Search Tool (BLAST) (Altschul et al., *J. Mol. Biol.* 215:403, 1990) is available from several sources, including the National Center for Biotechnology Information (NCBI, Bethesda, Md.) and on the internet, for use in connection with the sequence analysis programs blastp, blastn, blastx, tblastn and tblastx. A description of how to determine sequence identity using this program is available on the NCBI website on the internet.

Homologs and variants of an antibody that specifically bind a polypeptide are typically characterized by possession of at least about 75%, for example at least about 80%, 90%, 95%, 96%, 97%, 98% or 99% sequence identity counted over the full-length alignment with the amino acid sequence of the antibody using the NCBI Blast 2.0, gapped blastp set to default parameters. For comparisons of amino acid sequences of greater than about 30 amino acids, the Blast 2 sequences function is employed using the default BLOSUM62 matrix set to default parameters, (gap existence cost of 11, and a per residue gap cost of 1). When aligning short peptides (fewer than around 30 amino acids), the alignment should be performed using the Blast 2 sequences function, employing the PAM30 matrix set to default parameters (open gap 9, extension gap 1 penalties). Proteins with even greater similarity to the reference sequences will show increasing percentage identities when assessed by this method, such as at least 80%, at least 85%, at least 90%, at least 95%, at least 98%, or at least 99% sequence identity. When less than the entire sequence is being compared for sequence identity, homologs and variants will typically possess at least 80% sequence identity over short windows of 10-20 amino acids, and may possess sequence identities of at least 85% or at least 90% or 95% depending on their similarity to the reference sequence. Methods for determining sequence identity over such short windows are available at the NCBI website on the internet. One of skill in the art will appreciate that these sequence identity ranges are provided for guidance only; it is entirely possible that strongly significant homologs could be obtained that fall outside of the ranges provided.

Subject: Living multi-cellular vertebrate organisms, a category that includes both human and veterinary subjects, including human and non-human mammals.

Synthetic: Produced by artificial means in a laboratory, for example a synthetic nucleic acid or protein (for example, an antibody) can be chemically synthesized in a laboratory.

Therapeutically effective amount: A quantity of a specific substance sufficient to achieve a desired effect in a subject being treated. For instance, this can be the amount necessary to inhibit, suppress or eliminate a *Y. pestis* infection. In one embodiment, a therapeutically effective amount is the amount necessary to eliminate the infection or prevent the spread of the infection. When administered to a subject, a dosage will generally be used that will achieve target tissue concentrations that have been shown to achieve a desired in vitro effect.

Vector: A nucleic acid molecule as introduced into a host cell, thereby producing a transformed host cell. A vector may include nucleic acid sequences that permit it to replicate in a host cell, such as an origin of replication. A vector may also include one or more selectable marker genes and other genetic elements known in the art.

III. High Affinity Monoclonal Antibodies Specific for *Yersinia pestis* F1 Antigen Disclosed herein are two human monoclonal antibodies that specifically bind the F1 antigen of *Y. pestis*, the causative agent of plague, with high (picomolar) affinity. The disclosed antibodies were generated by affinity maturation of two scFv clones isolated from a human scFv phage display library. These human antibodies bind different epitopes of the F1 antigen and retain immunoreactivity upon chemical conjugation to metal chelators, enzymes and large fluorophores. These features are advantageous for a number of uses, including diagnostic and therapeutic applications.

Monoclonal antibodies that specifically bind *Y. pestis* F1 antigen are provided. In some embodiments, the monoclonal antibody includes a variable light (VL) domain and a variable heavy (VH) domain and possesses the CDR sequences of antibody AM IgG B or AM IgG H, as disclosed herein. In some examples, the VL domain comprises the complementarity determining region 1 (CDR1), CDR2 and CDR3 sequences of SEQ ID NO: 1 and the VH domain comprises the CDR1, CDR2 and CDR3 sequences of SEQ ID NO: 2. In other examples, the VL domain comprises the CDR1, CDR2 and CDR3 sequences of SEQ ID NO: 3 and the VH domain comprises the CDR1, CDR2 and CDR3 sequences of SEQ ID NO: 4.

The CDR sequences can be determined using any convention known in the art, such as the Kabat, IMGT or Chothia method. In some embodiments, the VL domain CDR1, CDR2 and CDR3 sequences respectively comprise residues 23-33, 49-55 and 88-96 of SEQ ID NO: 1 and the VH domain CDR1, CDR2 and CDR3 sequences respectively comprise residues 26-35, 52-60 and 100-108 of SEQ ID NO: 2. In other embodiments, the VL domain CDR1, CDR2 and CDR3 sequences respectively comprise residues 24-34, 50-56 and 90-97 of SEQ ID NO: 3 and the VH domain CDR1, CDR2 and CDR3 sequences respectively comprise residues 26-35, 52-59 and 98-104 of SEQ ID NO: 4.

In some examples, the amino acid sequence of the VL domain is at least 90%, at least 91%, at least 92%, at least 93%, at least 94%, at least 95%, at least 96%, at least 97%, at least 98% or at least 99% identical to residues 1-107 of SEQ ID NO: 1; and/or the amino acid sequence of the VH domain is at least 90%, at least 91%, at least 92%, at least 93%, at least 94%, at least 95%, at least 96%, at least 97%, at least 98% or at least 99% identical to residues 1-119 of SEQ ID NO: 2. In specific non-limiting examples, the amino acid sequence of the VL domain comprises or consists of residues 1-107 of SEQ ID NO: 1; and/or the amino acid sequence of the VH domain comprises or consists of residues 1-119 of SEQ ID NO: 2.

In other examples, the amino acid sequence of the VL domain is at least 90%, at least 91%, at least 92%, at least 93%, at least 94%, at least 95%, at least 96%, at least 97%, at least 98% or at least 99% identical to residues 1-106 of SEQ ID NO: 3; and/or the amino acid sequence of the VH domain is at least 90%, at least 91%, at least 92%, at least 93%, at least 94%, at least 95%, at least 96%, at least 97%, at least 98% or at least 99% identical to residues 1-115 of SEQ ID NO: 4. In specific non-limiting examples, the amino acid sequence of the VL domain comprises or consists of residues 1-106 of SEQ ID NO: 3; and/or the amino acid sequence of the VH domain comprises or consists of residues 1-115 of SEQ ID NO: 4.

In some embodiments, the monoclonal antibody is an antigen-binding fragment selected from an Fab fragment, an Fab' fragment, an F(ab)'$_2$ fragment, a single chain variable fragment (scFv) and a disulfide stabilized variable fragment (dsFv). In particular examples, the monoclonal antibody is an scFv.

In other embodiments, the monoclonal antibody is an IgG, such as an IgG1. In some examples, the monoclonal antibody has a light chain comprising an amino acid sequence at least 90%, at least 91%, at least 92%, at least 93%, at least 94%, at least 95%, at least 96%, at least 97%, at least 98% or at least 99% identical SEQ ID NO: 1; and/or a heavy chain comprising an amino acid sequence at least 90%, at least 91%, at least 92%, at least 93%, at least 94%, at least 95%, at least 96%, at least 97%, at least 98% or at least 99% identical to SEQ ID NO: 2. In non-limiting examples, the light chain comprises the amino acid sequence of SEQ ID NO: 1; and/or the heavy chain comprises the amino acid sequence of SEQ ID NO: 2. In other examples, the monoclonal antibody has a light chain comprising an amino acid sequence at least 90%, at least 91%, at least 92%, at least 93%, at least 94%, at least 95%, at least 96%, at least 97%, at least 98% or at least 99% identical SEQ ID NO: 3; and/or a heavy chain comprising an amino acid sequence at least 90%, at least 91%, at least 92%, at least 93%, at least 94%, at least 95%, at least 96%, at least 97%, at least 98% or at least 99% identical to SEQ ID NO: 4. In non-limiting examples, the light chain comprises the amino acid sequence of SEQ ID NO: 3; and/or the heavy chain comprises the amino acid sequence of SEQ ID NO: 4. In specific examples, the heavy or light chain is modified with an unnatural amino acid (UAA), such as N6-(2-azidoethoxy)-carbonyl-L-lysine (PyL). The UAA can be inserted, for example, in the constant region of the light chain for site-specification conjugation. As one example, AM IgG B can include a Ser209Pyl modification (with respect to SEQ ID NO: 1). As another example, AM IgG H can include a Lys161Pyl modification (with respect to SEQ ID NO: 3).

In some embodiments, the monoclonal antibody is a fully human antibody. In other embodiments, the monoclonal antibody is a humanized or chimeric antibody.

Also provided are immunoconjugates that include a monoclonal antibody disclosed herein and an effector molecule. In some embodiments, the effector molecule is a detectable label or a radionuclide. In some examples, the detectable label comprises a fluorophore, an enzyme or a radioisotope. In some examples, the immunoconjugate comprises a chelator and the radionuclide is bound to the chelator. Examples of radionuclides include, but are not limited to, $^{99m}$Tc, $^{111}$In, $^{228}$Ac, $^{211}$At, $^{119}$Sb, $^{97}$Ru, $^{64}$Cu, $^{67}$Ga, $^{68}$Ga, $^{72}$As, $^{89}$Zr, $^{90}$Y and $^{201}$Tl. Other possible radionuclides include $^{225}$Ac and its daughters, $^{227}$Th and its daughters, $^{47}$Sc, and $^{47}$Sc.

One of skill in the art is capable of selecting an appropriate chelator for a selected radionuclide. Examples of polyaza linear and macrocyclic chelators with a variety of pendant coordinating groups include, but are not limited to, diethylene-triamine-pentaacetic acid (DTPA), cyclohexane-diethylene-triamine-pentaacetic-acid (CHX-DTPA), DTPA derivatives such as p-isothiocyanatobenzyl-diethylenetri-aminepentaacetic acid (p-SCN-Bz-DTPA), ethylenedi-amine-tetraacetic acid (EDTA), 1,4,7,10-tetraazacyclodode-cane-1,4,7,10-tetraacetic acid (DOTA), 1,4,7,10-tetraazacyclododecane-1,4,7,10-phosphonic acid (DOTP), DOTA derivatives such as p-isothiocyanatobenzyl-1,4,7,10-tetraazacyclododecane-1,4,7,10-tetraacetic acid (p-SCN-Bz-DOTA), 1,4,7-triazacyclononane-N,N',N"-triacetetate (NOTA), ethylenediamine tetra(methylene phosphonic acid) (EDTMP), 1,4,7,10-tetraazacyclododecane-1,4,7,10-tetra (methylene phosphonic acid) (DOTMP), N-chloro-p-toluenesulfonamide, tetrachloro-3-6α-diphenylglycouril-3, (2-(4-isothiocyanatobenzyl-1,4,7,10-tetraaza-1,4,7,10,tetra-(2-carbamonyl-methyl)-cyclododecane) (TCMC), tris (hydroxypyridinone) (THP) and desferrioxamine (DFO). Biorthogonal derivatives of 1,4,7,10-tetraazacyclodode-cane-1,4,7,-triacetic acid (DO3A) and 1,4,7,10-tetraazacy-clododecane-1,7-diacetic acid (DO2A) and the phosphonic acid equivalents are also possible.

Further provided are fusion proteins that include a monoclonal antibody disclosed herein and a heterologous protein or peptide. In some embodiments, the heterologous protein is a fluorescent protein, such as a green fluorescent protein (GFP). In some examples, the GFP is a superfolder GFP fused between the heavy and light chains of the antibody (referred to herein as "scFp").

Also provided herein are nucleic acid molecules encoding the disclosed monoclonal antibodies and fusion proteins. In some examples, the nucleic acid molecule is operably linked to a promoter. Vectors comprising the nucleic acid molecules are also provided.

Further provided are compositions that include a monoclonal antibody, immunoconjugate or fusion protein disclosed herein, and a pharmaceutically acceptable carrier.

Methods of treating a *Yersinia pestis* infection and/or plague in a subject are also provided herein. In some embodiments, the method includes administering to the subject a therapeutically effective amount of a monoclonal antibody, immunoconjugate, fusion protein or composition disclosed herein.

Methods of detecting F1 antigen, or F1-expressing *Y. pestis*, in a sample are further provided herein. In some embodiments, the method includes contacting a sample, such as a biological sample, with a monoclonal antibody or immunoconjugate disclosed herein; and detecting binding of the monoclonal antibody or the immunoconjugate to the sample. In some examples, the biological sample comprises a blood, serum, lymph node aspirate or sputum sample. In other examples, the sample is an environmental sample, for example food, water, or other materials that may contain or be contaminated with *Y. pestis*. In some embodiments, detection of the F1 antigen or F1-expressing *Y. pestis* is performed by lateral flow assay (LFA) using an anti-F1 antibody disclosed herein.

Further provided are methods of diagnosing a subject as having a *Yersinia pestis* infection. In some embodiments, the method includes contacting a biological sample obtained from the subject with a monoclonal antibody or immunoconjugate disclosed herein; and detecting binding of the monoclonal antibody or the immunoconjugate to the sample. In some examples, the biological sample comprises a blood, serum, lymph node aspirate or sputum sample. In other examples, the sample is from a carrier of *Y. pestis*, such a rodent or a flea. In some embodiments, diagnosis of *Y. pestis* is performed by lateral flow assay (LFA) using an anti-F1 antibody disclosed herein. In additional examples, the methods include administering to the subject a therapeutically effective amount of a monoclonal antibody, immunoconjugate, fusion protein or composition disclosed herein and/or one or more antibiotics.

The following examples are provided to illustrate certain particular features and/or embodiments. These examples should not be construed to limit the disclosure to the particular features or embodiments described.

EXAMPLES

Example 1: Binding Specificity of Anti-F1 Monoclonal Antibodies

This example describes binding specificity of two monoclonal antibodies that target *Y. pestis* F1 antigen (see also Lillo et al., *PLoS ONE* 6(12): e27756, 2011). The results demonstrated that the two antibodies, IgG B and IgG H, specifically bind the F1 antigen with high affinity, but bind different epitopes of F1.

FIGS. 1A-1B show antibody specificity for F1-positive *Y. pestis*. Flow cytometry analysis and genetic analysis of a mixed bacterial community demonstrated that the IgG B and IgG H antibodies target *Y. pestis* selectively. In this study, a mixed population of *E. coli, Y. pseudotuberculosis, B. anthracis*, P. fluorescence and *Y. pestis* was stained with phycoerythrin-labelled anti-F1 IgG B. The percentage of stained cells (11.3%) matched *Y. pestis* representation (10%) within error (FIG. 1A). Furthermore, single PE-labelled cells tested positive by PCR amplification of *Y. pestis*-specific genomic region YpA, whereas unstained cells did not. Similar results were obtained with antibody IgG H.

In addition, enzyme-linked immunosorbent assay (ELISA) analysis of a mixed community confirmed specificity of the antibodies for *Y. pestis*. Samples of the same mixed community with different *Y. pestis* representation was analyzed by whole-cell ELISA. ELISA signals (absorbance at 450 nm caused by antibody binding) were directly proportional to the number of *Y. pestis* in the mixed community. A minimum of one thousand cells corresponding to 0.4% of the entire population could be detected.

Figure 2B:
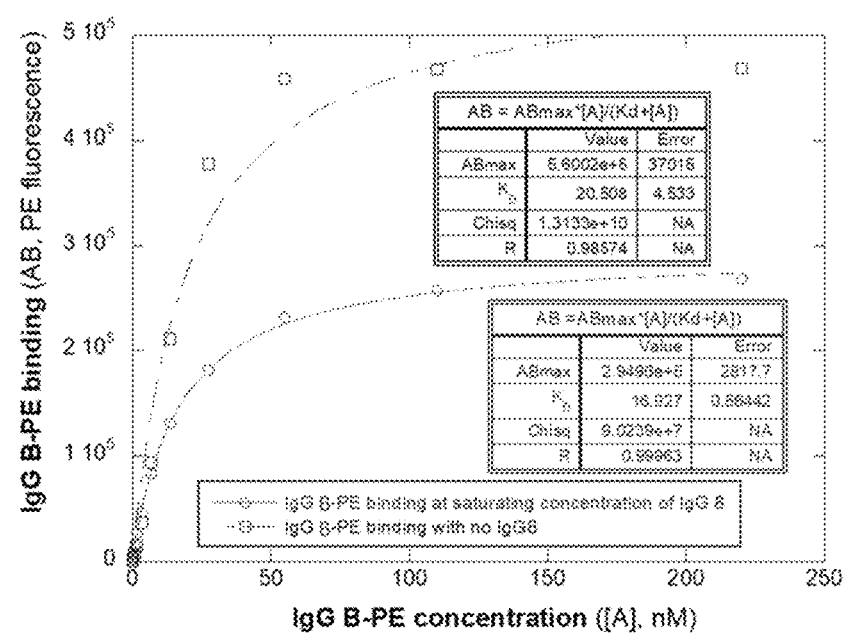
Figure 2C:
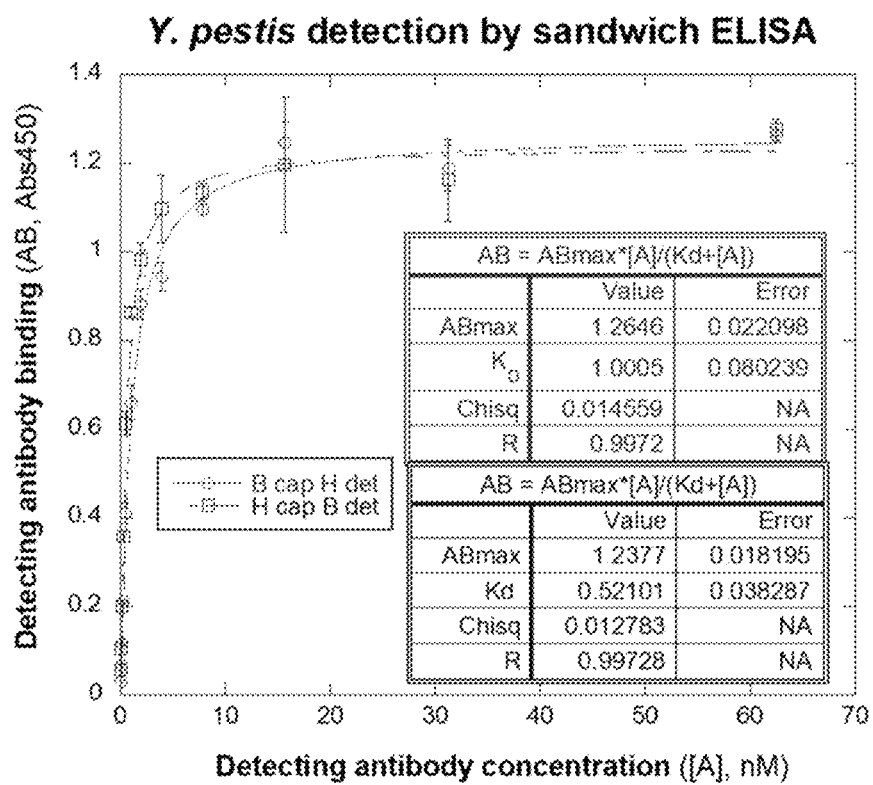

The results shown in FIGS. 2A-2C demonstrate that the IgG B and IgG H antibodies target two different epitopes of the F1 antigen. The binding of antibody IgG B and antibody IgG H to purified or cell-expressed F1 was non-competitive, as shown by fluorescence-linked immunosorbent assay (FLISA) (FIG. 2A), flow cytometry (FIG. 2B), and sandwich ELISA (FIG. 2C). Intrinsically fluorescent scFp B (antibody B single chain (scFv)-GFP chimera) bound to purified antigen F1 was not displaced by IgG H but it is by IgG B (FIG. 2A). IgG B-PE bound to *Y. pestis* with the same affinity (same Kd, within error) in the presence or absence of saturating concentration of unlabeled IgG H (FIG. 2B). However, the maximum amount of antibody binding was reduced, possibly due to the steric hinderance of the bulky PE. Steric hinderance could also explain why IgG B-PE has a lower affinity (higher $K_D$) for *Y. pestis* than the unconjugated counterpart (see Table 1 below). Cells captured by immobilized IgG B or IgG H and saturated with the same antibody still bound to HRP conjugated antibody IgG H or antibody IgG B, respectively, albeit with lower affinity (higher $K_D$) than their unconjugated counterpart (FIG. 2C). Again, this result might be due to steric hinderance of the attached HRP. In support of this idea, the reduction in affinity was much less pronounced for antibodies conjugated to HRP than for antibodies conjugated to PE, which are 5-times larger than HRP.

Figure 3:
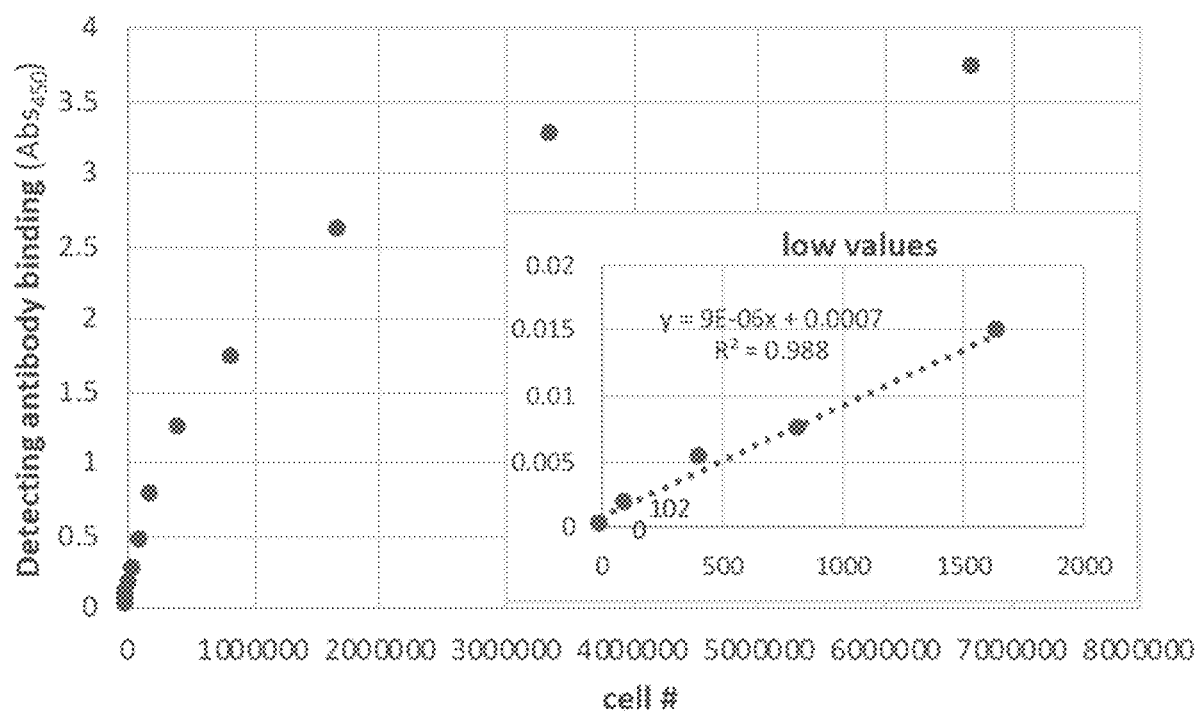
FIG. 3: Sensitivity of *Y. pestis* detection by sandwich ELISA. As few at 102 cells can be detected by sandwich ELISA where cells are captured by IgG H and detected by IgG B-HRP conjugate.

The results shown in FIG. 3 demonstrate that using IgG B and IgG H in a sandwich ELISA results in high sensitivity of *Y. pestis* detection. As few at 102 cells could be detected by sandwich ELISA where cells are captured by IgG H and detected by IgG B-HRP conjugate.

The IgG B and IgG H antibodies are further described in Lillo et al. ("Development of Anti-*Y. Pestis* Human Antibodies with Features Required for Diagnostic and Therapeutic Applications," *Immunotargets Ther*, submission ID 267077, pre-press).

Example 2: High Affinity Monoclonal Antibodies that Bind *Y. pestis* F1 Antigen

This example describes two affinity matured monoclonal antibodies that specifically bind the F1 antigen of *Y. pestis*. The affinity matured (AM) antibodies, referred to herein as AM IgG B and AM IgG H, are based on previously developed scFv clones specific for F1 (Example 1; and Lillo et al., *PLoS ONE* 6(12): e27756, 2011).

The light and heavy chains of the two antibodies are provided below. CDR sequences of each antibody are shown in bold; mutations introduced during affinity maturation are underlined.

(SEQ ID NO: 1)
AM IgG B light chain
DIRMTQSPSSLSASVGDRVTITCRASRSISGYLNWYQQKPGKAPKLLIY

ATSSLQSGVPSRFSGSGSGTDFTLTISSLQPEDFATYYCQQSYSTPSSF

GQGTKVDIKRTVAAPSVFIFPPSDEQLKSGTASVVCLLNNFYPREAKVQ

WKVDNALQSGNSQESVTEQDSKDSTYSLSSTLTLSKADYEKHKVYACEV

THQGLSSPVTKSFNRGEC (SEQ ID NO: 2)
AM IgG B heavy chain
QVQLVESGGGLVKPGGSLRLSCAASGFTFSDYYMSWIRQAPGKGLEWVS

YISGSGSIIYYADSVKGRFTISRDNAKNSLYLQMNSLRAEDTAVYYCAK

-continued

EIRKHDAFDIWGQGTMVTVSSASTKGPSVFPLAPSSKSTSGGTAALGCL

VKDYFPEPVTVSWNSGALTSGVHTFPAVLQSSGLYSLSSVVTVPSSSLG

TQTYICNVNHKPSNTKVDKKVEPKSCDKTHTCPPCPAPELLGGPSVFLF

PPKPKDTLMISRTPEVTCVVVDVSHEDPEVKFNWYVDGVEVHNAKTKPR

EEQYNSTYRVVSVLTVLHQDWLNGKEYKCKVSNKALPAPIEKTISKAKG

QPREPQVYTLPPSRDELTKNQVSLTCLVKGFYPSDIAVEWESNGQPENN

YKTTPPVLDSDGSFFLYSKLTVDKSRWQQGNVFSCSVMHEALHNHYTQK

SLSLSPGK (SEQ ID NO: 3)
AM IgG H light chain
QPVLTQSPSVSVSPGQTASITCSGDKLGGRYASWYQQKPGQSPVLVIYQ

DTKRPSGIPERFSGSNSGNTATLTISGTQAMDEADYYCQSWDSSAAVFG

TGTKLTVLGQPKAAPSVTLFPPSSEELQANKATLVCLISDFYPGAVTVA

WKADSSPVKAGVETTTPSKQSNNKYAASSYLSLTPEQWKSHKSYSCQVT

HEGSTVEKTVAPTECS (SEQ ID NO: 4)
AM IgG H heavy chain
QVQLQQWGAGLLKPSETLSLTCAVYGGSFSGYYWSWIRQPPGKGLEWIG

EINRSGNTNYNPSLKSRVTISVDTSKNQFSLQLNSVTPEDTAVYYCART

RGYFDLWGRGTLVTVSSASTKGPSVFPLAPSSKSTSGGTAALGCLVKDY

FPEPVTVSWNSGALTSGVHTFPAVLQSSGLYSLSSVVTVPSSSLGTQTY

ICNVNHKPSNTKVDKKVEPKSCDKTHTCPPCPAPELLGGPSVFLFPPKP

KDTLMISRTPEVTCVVVDVSHEDPEVKFNWYVDGVEVHNAKTKPREEQY

NSTYRVVSVLTVLHQDWLNGKEYKCKVSNKALPAPIEKTISKAKGQPRE

PQVYTLPPSRDELTKNQVSLTCLVKGFYPSDIAVEWESNGQPENNYKTT

PPVLDSDGSFFLYSKLTVDKSRWQQGNVFSCSVMHEALHNHYTQKSLSL

SPGK

Binding affinity of the affinity matured antibodies to the F1 antigen was tested and compared to the original IgG B and IgG H antibodies and a commercially available antibody (YP19). The results demonstrate that the affinity matured antibodies exhibit increased binding affinity compared to their non-matured counterparts and the commercial antibody (Table 1).

TABLE 1

Affinities of F1-specific antibodies for cell-expressed F1 antigen

| Antibody | Affinity ($K_D$, nM) | F1-specific Abs vs commercial antibody (YP19 Kd/F1 Ab Kd) |
| --- | --- | --- |
| IgGB | 0.23 + 0.02 | 16.7 |
| AM$^a$ IgG B | 0.09 + 0.08 | 41.6 |
| IgG H | 0.08 + 0.005 | 48.5 |
| AM$^a$ IgG H | 0.03 + 0.007 | 127.7 |
| Commercial YP19 | 3.83 + 0.39 | 1 |

$^a$Affinity Matured

Example 3: Development of a Lateral Flow Assay for Detection of Plague

This example describes the development and optimization of a lateral flow assay for detection of *Y. pestis* F1 antigen using affinity matured anti-F1 antibodies.

To optimize conjugation of anti-F1 antibody to colloidal gold nanoparticles, a variety of conjugation conditions were evaluated, including various pH values, antibody concentrations and antibody:colloidal gold ratios. The results demonstrated that antibody concentrations ranging from 30 mM to 100 mM and pH values from 8 to 8.5 allowed for the greatest conjugation efficiency.

Next, a variety of nitrocellulose membranes were tested using an antibody concentration of 55 mM and conjugation at pH 8.5. The three best nitrocellulose membrane performers were CN95 IUN95ER, CN140 IUN14ER, and FF170HP (DNC Diagnostics), in decreasing order of positive control signal intensity.

Figure 4A:
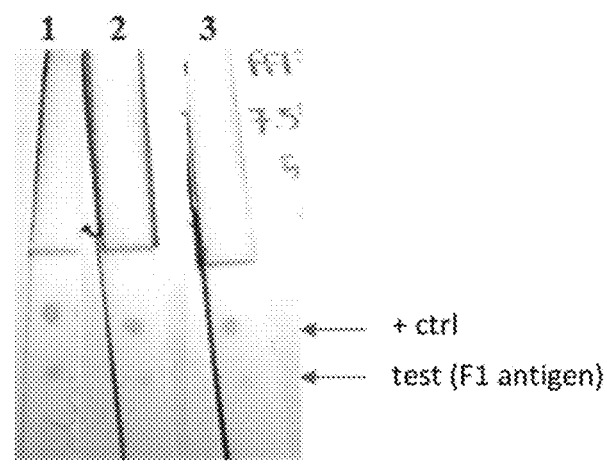
FIGS. 4A-4B: Limit of detection of plague lateral flow assay (LFA). Various quantities of F1 antigen (FIG. 4A) and *Y. pestis* cells (FIG. 4B) were analyzed using a nitrocellulose membrane spotted with 65 ng of anti-human antibody (positive control spot) and 1 µg of AM IgG H (test spot). The results demonstrate that the LFA was capable of detecting as little as 5 ng F1 and 7×10⁴ *Y. pestis* cells.
Figure 4B:
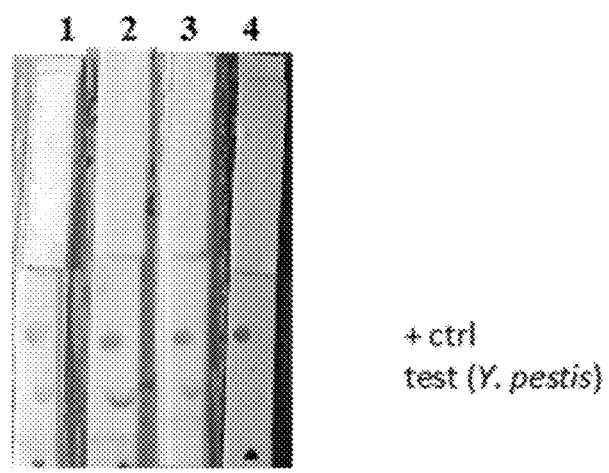

A lateral flow assay was carried out to test the limit of detection using various amounts of F1 antigen (5 ng, 7 ng and 10 ng) and *Y. pestis* cells ($3.5 \times 10^5$, $2 \times 10^5$, $1 \times 10^5$, and $7 \times 10^4$). The assay was performed using membrane FF170HP 10547005, spotted with 65 ng of anti-human antibody (positive control spot, top spot in FIGS. 4A-4B) and 1 µg of AM IgG H (F1-capturing antibody, test spot, bottom spot in FIGS. 4A-4B). The results demonstrated that the assay could detect the lowest antigen concentrations tested (i.e., 5 ng of F1 antigen and $7 \times 10^4$ F1-expressing *Y. pestis* cells).

Example 4: Antibody Stability by Dynamic Light Scattering (DLS) Analysis

This example describes a study to evaluate stability of affinity matured antibodies AM IgG B and AM IgG H using DLS.

Figure 5A:
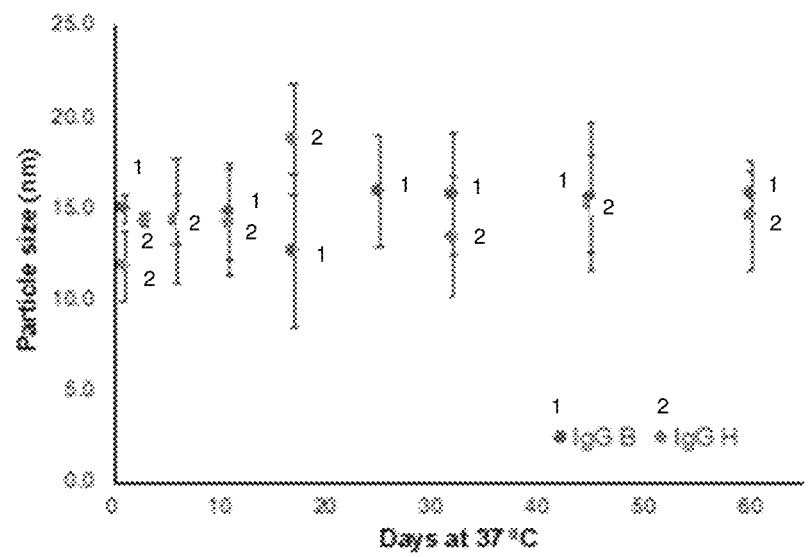
FIGS. 5A-5B: Stability of AM IgG B and AM IgG H antibodies by dynamic light scattering (DLS).

Antibodies were dissolved in phosphate buffered saline (PBS) at a concentration of 0.9 mg/mL in the absence of preservatives, incubated at 37° C., and regularly analyzed for particle size by DLS over a period of 90 days. The particle diameter did not change for either of the antibodies during this time, indicating a lack of aggregation and demonstrating the stability of the antibodies (FIG. 5A).

Figure 5B:
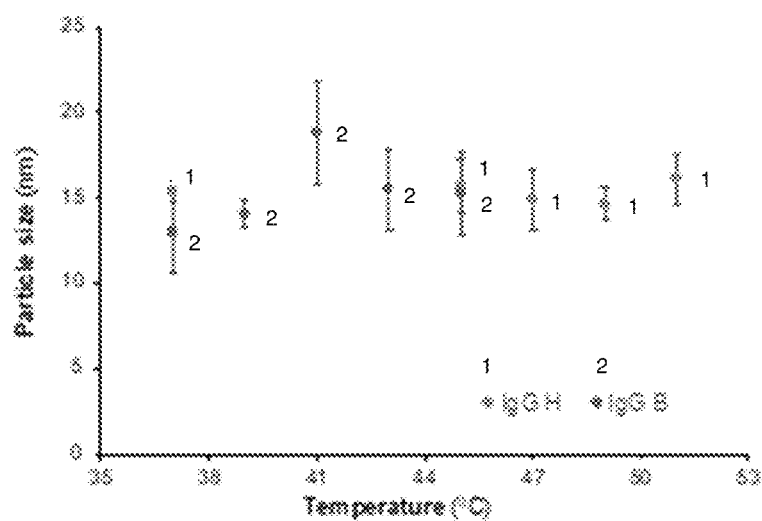

Antibody solutions (0.74 and 1.7 mg/mL in PBS for AM IgG B and AM IgG H, respectively) were also subjected to equilibration at different temperatures to determine which temperature caused a loss of DLS signal. Since the antibody concentration used was the minimum needed for detection of 15 nm particles, the loss of signal signifies lower concentration of higher diameter particles, which in turn reveals protein aggregation. The results demonstrated that the aggregating temperature was 45° C. for AM IgG B and 51° C. for AM IgG H (FIG. 5B).

Example 5: Efficacy of AM IgG B and AM IgG H in Mouse Plague Models

To test for therapeutic effect in vivo, the affinity matured anti-F1 antibodies are evaluated in a prophylaxis challenge model of plague. BALB/c mice are administered AM IgG B or AM IgG H at a dose of approximately 500 µg. Mice are then challenged with either the CO92 or C12 strain of *Y. pestis*. After 20 days, serology, gross necropsies (to include confirmation of sterile immunity) and histopathological analyses will be performed. It is expected that animals treated with antibodies will exhibit either no symptoms or reduced symptoms, with respect to untreated animals. It is also expected that a lower bacterial titer will be detected in spleen homogenate samples of treated animals.

In view of the many possible embodiments to which the principles of the disclosed subject matter may be applied, it should be recognized that the illustrated embodiments are only preferred examples of the disclosure and should not be taken as limiting the scope of the disclosure. Rather, the scope of the disclosure is defined by the following claims. We therefore claim all that comes within the scope and spirit of these claims.

The invention claimed is:

1. A monoclonal antibody that specifically binds *Yersinia pestis* F1 antigen, comprising a variable light (VL) domain and a variable heavy (VH) domain, wherein:
   the VL domain comprises the complementarity determining region 1 (CDR1), CDR2 and CDR3 sequences of SEQ ID NO: 1 and the VH domain comprises the CDR1, CDR2 and CDR3 sequences of SEQ ID NO: 2; or
   the VL domain comprises the CDR1, CDR2 and CDR3 sequences of SEQ ID NO: 3 and the VH domain comprises the CDR1, CDR2 and CDR3 sequences of SEQ ID NO: 4.

2. The monoclonal antibody of claim 1, wherein the CDR sequences are determined using the method of Kabat, IMGT or Chothia.

3. The monoclonal antibody of claim 1, wherein:
   the VL domain CDR1, CDR2 and CDR3 sequences respectively comprise residues 23-33, 49-55 and 88-96 of SEQ ID NO: 1 and the VH domain CDR1, CDR2 and CDR3 sequences respectively comprise residues 26-35, 52-60 and 100-108 of SEQ ID NO: 2; or
   the VL domain CDR1, CDR2 and CDR3 sequences respectively comprise residues 24-34, 50-56 and 90-97 of SEQ ID NO: 3 and the VH domain CDR1, CDR2 and CDR3 sequences respectively comprise residues 26-35, 52-59 and 98-104 of SEQ ID NO: 4.

4. The monoclonal antibody of claim 3, wherein:
   the amino acid sequence of the VL domain is at least 90% identical to residues 1-107 of SEQ ID NO: 1 and the amino acid sequence of the VH domain is at least 90% identical to residues 1-119 of SEQ ID NO: 2; or
   the amino acid sequence of the VL domain is at least 90% identical to residues 1-106 of SEQ ID NO: 3; and the amino acid sequence of the VH domain is at least 90% identical to residues 1-115 of SEQ ID NO: 4.

5. The monoclonal antibody of claim 4, wherein:
   the amino acid sequence of the VL domain comprises or consists of residues 1-107 of SEQ ID NO: 1 and the amino acid sequence of the VH domain comprises or consists of residues 1-119 of SEQ ID NO: 2; or
   the amino acid sequence of the VL domain comprises or consists of residues 1-106 of SEQ ID NO: 3 and the amino acid sequence of the VH domain comprises or consists of residues 1-115 of SEQ ID NO: 4.

6. The monoclonal antibody of claim 1, wherein the monoclonal antibody is an antigen-binding fragment selected from an Fab fragment, an Fab' fragment, an F(ab)'$_2$ fragment, a single chain variable fragment (scFv) and a disulfide stabilized variable fragment (dsFv).

7. The monoclonal antibody of claim 1, wherein the antibody is an IgG.

8. The monoclonal antibody of claim 7, comprising:
   a light chain comprising the amino acid sequence of SEQ ID NO: 1 and a heavy chain comprising the amino acid sequence of SEQ ID NO: 2; or
   a light chain comprising the amino acid sequence of SEQ ID NO: 3 and a heavy chain comprising the amino acid sequence of SEQ ID NO: 4.

9. The monoclonal antibody of claim 1, wherein the monoclonal antibody is a human antibody or a chimeric antibody.

10. An immunoconjugate comprising the monoclonal antibody of claim 1 and an effector molecule.

11. The immunoconjugate of claim 10, wherein the effector molecule is a detectable label or a radionuclide.

12. The immunoconjugate of claim 11, wherein the immunoconjugate comprises a chelator and the radionuclide is bound to the chelator.

13. The immunoconjugate of claim 12, wherein the chelator is diethylene-triamine-pentaacetic acid (DTPA), cyclohexane-diethylene-triamine-pentaacetic-acid (CHX-DTPA), p-isothiocyanatobenzyl-diethylenetriaminepentaacetic acid (p-SCN-Bz-DTPA), ethylenediamine-tetraacetic acid (EDTA), 1,4,7,10-tetraazacyclododecane-1,4,7,10-tetraacetic acid (DOTA), p-isothiocyanatobenzyl-1,4,7,10-tetraazacyclododecane-1,4,7,10-tetraacetic acid (p-SCN-Bz-DOTA), 1,4,7-triazacyclononane-N,N',N''-triacetetate (NOTA), ethylenediamine tetra(methylene phosphonic acid) (EDTMP), 1,4,7,10-tetraazacyclododecane-1,4,7,10-tetra (methylene phosphonic acid) (DOTMP), N-chloro-p-toluenesulfonamide, tetrachloro-3-6α-diphenylglycouril-3, (2-(4-isothiocyanatobenzyl-1,4,7,10-tetraaza-1,4,7,10,tetra-(2-carbamonyl-methyl)-cyclododecane) (TCMC), tris (hydroxypyridinone) (THP), or desferrioxamine (DFO).

14. The immunoconjugate of claim 12, wherein the radionuclide is $^{99m}$Tc, $^{123}$I, $^{125}$I, $^{131}$I, $^{111}$In, $^{97}$Ru, $^{64}$Cu, $^{67}$Ga, $^{68}$Ga, $^{72}$As, $^{89}$Zr, $^{90}$Y or $^{201}$Tl.

15. A fusion protein, comprising the monoclonal antibody of claim 1 and a heterologous protein or peptide.

16. An isolated nucleic acid molecule encoding the monoclonal antibody of claim 1.

17. A vector comprising the nucleic acid molecule of claim 16.

18. A host cell comprising the vector of claim 17.

19. A composition comprising the monoclonal antibody of claim 1 and a pharmaceutically acceptable carrier.

20. A method of treating a *Yersinia pestis* infection in a subject, comprising administering to the subject a therapeutically effective amount of the monoclonal antibody of claim 1, thereby treating the *Y. pestis* infection in the subject.

21. A method of detecting *Yersinia pestis* in a sample, comprising:
   contacting the sample with the monoclonal antibody of claim 1; and
   detecting binding of the monoclonal antibody to the sample, thereby detecting *Y. pestis* in the sample.

22. A method of detecting F1 antigen or an F1-expressing *Y. pestis* in a sample, comprising:
   contacting the sample with the monoclonal antibody of claim 1; and
detecting binding of the monoclonal antibody to the sample, thereby detecting F1 antigen or F1-expressing *Y. pestis* in the sample.

* * * * *

SEQUENCE LISTING

```
<160> NUMBER OF SEQ ID NOS: 4

<210> SEQ ID NO 1
<211> LENGTH: 214
<212> TYPE: PRT
<213> ORGANISM: Artificial Sequence
<220> FEATURE:
<223> OTHER INFORMATION: Synthetic polypeptide

<400> SEQUENCE: 1

Asp Ile Arg Met Thr Gln Ser Pro Ser Ser Leu Ser Ala Ser Val Gly
1               5                   10                  15

Asp Arg Val Thr Ile Thr Cys Arg Ala Ser Arg Ser Ile Ser Gly Tyr
                20                  25                  30

Leu Asn Trp Tyr Gln Gln Lys Pro Gly Lys Ala Pro Lys Leu Leu Ile
            35                  40                  45

Tyr Ala Thr Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Ser
                85                  90                  95

Ser Phe Gly Gln Gly Thr Lys Val Asp Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 2
<211> LENGTH: 449
<212> TYPE: PRT
<213> ORGANISM: Artificial Sequence
<220> FEATURE:
<223> OTHER INFORMATION: Synthetic polypeptide

<400> SEQUENCE: 2

Gln Val Gln Leu Val Glu Ser Gly Gly Gly Leu Val Lys Pro Gly Gly
1               5                   10                  15
```

```
Ser Leu Arg Leu Ser Cys Ala Ala Ser Gly Phe Thr Phe Ser Asp Tyr
         20                  25                  30

Tyr Met Ser Trp Ile Arg Gln Ala Pro Gly Lys Gly Leu Glu Trp Val
         35                  40                  45

Ser Tyr Ile Ser Gly Ser Gly Ser Ile Ile Tyr Tyr Ala Asp Ser Val
 50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                 85                  90                  95

Ala Lys Glu Ile Arg Lys His Asp Ala Phe Asp Ile Trp Gly Gln Gly
                100                 105                 110

Thr Met Val Thr Val Ser Ser Ala Ser Thr Lys Gly Pro Ser Val Phe
             115                 120                 125

Pro Leu Ala Pro Ser Ser Lys Ser Thr Ser Gly Gly Thr Ala Ala Leu
     130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                 165                 170                 175

Gln Ser Ser Gly Leu Tyr Ser Leu Ser Ser Val Val Thr Val Pro Ser
             180                 185                 190

Ser Ser Leu Gly Thr Gln Thr Tyr Ile Cys Asn Val Asn His Lys Pro
         195                 200                 205

Ser Asn Thr Lys Val Asp Lys Lys Val Glu Pro Lys Ser Cys Asp Lys
     210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                 245                 250                 255

Arg Thr Pro Glu Val Thr Cys Val Val Val Asp Val Ser His Glu Asp
             260                 265                 270

Pro Glu Val Lys Phe Asn Trp Tyr Val Asp Gly Val Glu Val His Asn
         275                 280                 285

Ala Lys Thr Lys Pro Arg Glu Glu Gln Tyr Asn Ser Thr Tyr Arg Val
     290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                 325                 330                 335

Thr Ile Ser Lys Ala Lys Gly Gln Pro Arg Glu Pro Gln Val Tyr Thr
             340                 345                 350

Leu Pro Pro Ser Arg Asp Glu Leu Thr Lys Asn Gln Val Ser Leu Thr
         355                 360                 365

Cys Leu Val Lys Gly Phe Tyr Pro Ser Asp Ile Ala Val Glu Trp Glu
     370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                 405                 410                 415

Ser Arg Trp Gln Gln Gly Asn Val Phe Ser Cys Ser Val Met His Glu
             420                 425                 430
```

-continued

Ala Leu His Asn His Tyr Thr Gln Lys Ser Leu Ser Leu Ser Pro Gly
            435                 440                 445

Lys

<210> SEQ ID NO 3
<211> LENGTH: 212
<212> TYPE: PRT
<213> ORGANISM: Artificial Sequence
<220> FEATURE:
<223> OTHER INFORMATION: Synthetic polypeptide

<400> SEQUENCE: 3

Gln Pro Val Leu Thr Gln Ser Pro Ser Val Ser Val Ser Pro Gly Gln
1               5                   10                  15

Thr Ala Ser Ile Thr Cys Ser Gly Asp Lys Leu Gly Gly Arg Tyr Ala
            20                  25                  30

Ser Trp Tyr Gln Gln Lys Pro Gly Gln Ser Pro Val Leu Val Ile Tyr
        35                  40                  45

Gln Asp Thr Lys Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Met
65                  70                  75                  80

Asp Glu Ala Asp Tyr Tyr Cys Gln Ser Trp Asp Ser Ser Ala Ala Val
                85                  90                  95

Phe Gly Thr Gly Thr Lys Leu Thr Val Leu Gly Gln Pro Lys Ala Ala
            100                 105                 110

Pro Ser Val Thr Leu Phe Pro Pro Ser Ser Glu Glu Leu Gln Ala Asn
        115                 120                 125

Lys Ala Thr Leu Val Cys Leu Ile Ser Asp Phe Tyr Pro Gly Ala Val
    130                 135                 140

Thr Val Ala Trp Lys Ala Asp Ser Ser Pro Val Lys Ala Gly Val Glu
145                 150                 155                 160

Thr Thr Thr Pro Ser Lys Gln Ser Asn Asn Lys Tyr Ala Ala Ser Ser
                165                 170                 175

Tyr Leu Ser Leu Thr Pro Glu Gln Trp Lys Ser His Lys Ser Tyr Ser
            180                 185                 190

Cys Gln Val Thr His Glu Gly Ser Thr Val Glu Lys Thr Val Ala Pro
        195                 200                 205

Thr Glu Cys Ser
    210

<210> SEQ ID NO 4
<211> LENGTH: 445
<212> TYPE: PRT
<213> ORGANISM: Artificial Sequence
<220> FEATURE:
<223> OTHER INFORMATION: Synthetic polypeptide

<400> SEQUENCE: 4

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Pro Pro Gly Lys Gly Leu Glu Trp Ile
        35                  40                  45

Gly Glu Ile Asn Arg Ser Gly Asn Thr Asn Tyr Asn Pro Ser Leu Lys
    50                  55                  60

```
Ser Arg Val Thr Ile Ser Val Asp Thr Ser Lys Asn Gln Phe Ser Leu
 65                  70                  75                  80

Gln Leu Asn Ser Val Thr Pro Glu Asp Thr Ala Val Tyr Tyr Cys Ala
                 85                  90                  95

Arg Thr Arg Gly Tyr Phe Asp Leu Trp Gly Arg Gly Thr Leu Val Thr
            100                 105                 110

Val Ser Ser Ala Ser Thr Lys Gly Pro Ser Val Phe Pro Leu Ala Pro
        115                 120                 125

Ser Ser Lys Ser Thr Ser Gly Gly Thr Ala Ala Leu Gly Cys Leu Val
    130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Gln Thr Tyr Ile Cys Asn Val Asn His Lys Pro Ser Asn Thr Lys
        195                 200                 205

Val Asp Lys Lys Val Glu Pro Lys Ser Cys Asp Lys Thr His Thr Cys
210                 215                 220

Pro Pro Cys Pro Ala Pro Glu Leu Leu Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser His Glu Asp Pro Glu Val Lys
            260                 265                 270

Phe Asn Trp Tyr Val Asp Gly Val Glu Val His Asn Ala Lys Thr Lys
        275                 280                 285

Pro Arg Glu Glu Gln Tyr Asn Ser Thr Tyr Arg Val Val Ser Val Leu
290                 295                 300

Thr Val Leu His Gln Asp Trp Leu Asn Gly Lys Glu Tyr Lys Cys Lys
305                 310                 315                 320

Val Ser Asn Lys Ala Leu Pro Ala Pro Ile Glu Lys Thr Ile Ser Lys
                325                 330                 335

Ala Lys Gly Gln Pro Arg Glu Pro Gln Val Tyr Thr Leu Pro Pro Ser
            340                 345                 350

Arg Asp Glu Leu Thr Lys Asn Gln Val Ser Leu Thr Cys Leu Val Lys
        355                 360                 365

Gly Phe Tyr Pro Ser Asp Ile Ala Val Glu Trp Glu Ser Asn Gly Gln
370                 375                 380

Pro Glu Asn Asn Tyr Lys Thr Thr Pro Pro Val Leu Asp Ser Asp Gly
385                 390                 395                 400

Ser Phe Phe Leu Tyr Ser Lys Leu Thr Val Asp Lys Ser Arg Trp Gln
                405                 410                 415

Gln Gly Asn Val Phe Ser Cys Ser Val Met His Glu Ala Leu His Asn
            420                 425                 430

His Tyr Thr Gln Lys Ser Leu Ser Leu Ser Pro Gly Lys
        435                 440                 445
```